United States Patent [19]
Fuse et al.

[11] Patent Number: 5,666,952
[45] Date of Patent: Sep. 16, 1997

[54] TISSUE TRANSMITTED LIGHT SENSOR

[75] Inventors: Masayoshi Fuse; Takuo Aoyagi, both of Tokyo, Japan

[73] Assignee: Nihon Kohden Corporation, Tokyo, Japan

[21] Appl. No.: 643,944

[22] Filed: May 7, 1996

[30] Foreign Application Priority Data

May 8, 1995 [JP] Japan .................................. 7-109463

[51] Int. Cl.⁶ .................................................. A61B 5/00
[52] U.S. Cl. .......................... 128/633; 128/664; 128/665
[58] Field of Search ............................ 607/633; 128/633, 128/664–667, 639

[56] References Cited

U.S. PATENT DOCUMENTS

| | | | |
|---|---|---|---|
| 4,768,516 | 9/1988 | Stoddart et al. | 128/665 |
| 5,140,989 | 8/1992 | Lewis et al. | 128/665 |

FOREIGN PATENT DOCUMENTS

| | | |
|---|---|---|
| 0678277 | 10/1994 | European Pat. Off. . |
| 3910749 | 10/1990 | Germany . |
| 2103787 | 2/1983 | United Kingdom . |
| WO9115990 | 10/1991 | WIPO . |

*Primary Examiner*—Lee S. Cohen
*Assistant Examiner*—David M. Ruddy
*Attorney, Agent, or Firm*—Sughrue, Mion, Zinn, Macpeak & Seas

[57] ABSTRACT

A supporting shaft stands on an external auditory canal arm holding an LED. An attaching portion holding a PD is rotatably connected to one end of a holding arm. A column having a through hole 11b into which the supporting shaft is slidably inserted is fixed to the other end of the holding arm. The external auditory canal arm and the holding arm are connected to each other by a coil spring.

2 Claims, 3 Drawing Sheets

TISSUE TRANSMITTED LIGHT SENSOR

BACKGROUND OF THE INVENTION

1. Field of the invention

The invention relates to a tissue transmitted light sensor which detects a change of the quantity of transmitted light due to absorptive substances in the blood flowing through an arterial vascular of the subject, thereby detecting the pulse wave of the blood, and particularly to a tissue transmitted light sensor which detects the pulse wave on the basis of light transmitted through a tissue in the vicinity of the superficial temporal artery.

2. Related art

In order to measure the oxygen saturation of the blood of the subject or the cardiac output, the blood volume, etc. with injecting dye in the blood, pulse photometry is used. A known probe for the pulse photometry, is an optical sensor probe which is to be attached on an earlobe, an ear concha, a fingertip, or the like. In the probe, a light emitting unit such as an LED emits light and a light receiving unit such as a photo diode PD receives the light, thereby detecting absorptive substances in the blood flowing through an arterial vascular in the tissue in the vicinity of the attached part.

The conventional optical sensor probe configured as described above has a problem in that, in the case where the probe is attached on a fingertip, the flow rate of the blood is varied when vasomotor nerves are irritated by reflex due to hyper ventilation or an injection so that a measure value becomes unstable.

In the case where the probe is attached on an ear, a measure value is hardly affected by vasoconstriction due to reflex. In this case, however, there arises a problem in that the amplitude of the pulse wave is much lower than that in a fingertip and, particularly for a patient under general anesthesia or immediately after operation, the measurement cannot be stably conducted.

When the cardiac output, the blood volume, etc. are to be measured by using dye, the attachment of the probe may cause a blood flow impediment. This produces a problem in that the measurement accuracy and reproducibility are impaired. Furthermore, the clip method which is often used for attaching a probe to an earlobe has a defect that, when the subject moves, the probe easily swings and hence it is difficult to conduct the measurement stably and highly accurately, thereby easily producing a measurement error.

SUMMARY OF THE INVENTION

The invention has been conducted in view of the above-mentioned circumstances. It is an object of the invention to provide a tissue transmitted light sensor, which can prevent deviation due to the difference of the space in the ear concha of the subject, from occurring, and which can be stably attached to the subject.

In order to attain the object, the tissue transmitted light sensor of the invention is a sensor comprising: an external auditory canal arm which holds one of a light emitting unit and a light receiving unit, the external auditory canal arm adapted to be inserted into an external auditory canal of an ear of a subject; and an attaching portion which holds the other one of the light emitting unit and the light receiving unit, the attaching portion adapted to be attached on an outer face of a temporal artery in the vicinity of the ear, wherein the sensor further comprises: a supporting shaft which stands in the vicinity of one end of the external auditory canal arm; a holding arm which rotatably holds at one end the attaching portion and has a column at the other end, a through hole being formed in the column, the supporting shaft being inserted into the through hole so as to be slidable in an axial direction; and a spring which is wound around the supporting shaft so as to connect the external auditory canal arm with the holding arm.

In the tissue transmitted light sensor configured as described above, the external auditory canal arm and the holding arm are connected to each other via the supporting shaft so as to be slidable (movable) in an axial direction. Even when the space in the ear concha of the subject is different in size among individuals, the angle of the holding arm with respect to the external auditory canal arm is kept substantially constant so that the attaching portion held by the holding arm is prevented from slipping off, thereby enabling the sensor to be stably attached.

According to the present invention, the superficial temporal artery is prevented from being pressed by a cartilage in the vicinity of the external auditory canal so that a change of the quantity of transmitted light due to absorptive substances in the blood flowing through the artery can be stably detected without impeding the blood flow.

DETAILED DESCRIPTION OF THE PREFERRED EMBODIMENTS

Hereinafter, an embodiment of the tissue transmitted light sensor of the invention will be described with reference to the accompanying drawings.

Figure 1:
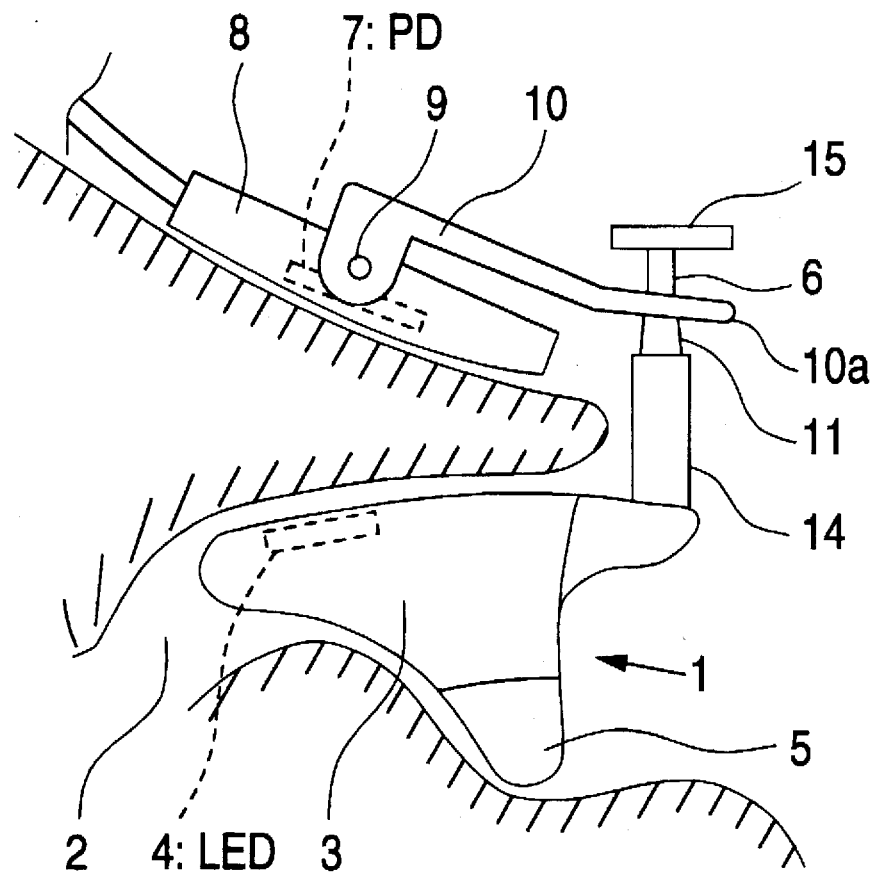
FIG. 1 is a diagram illustrating the attached state of an embodiment of the tissue transmitted light sensor of the invention.
Figure 2:
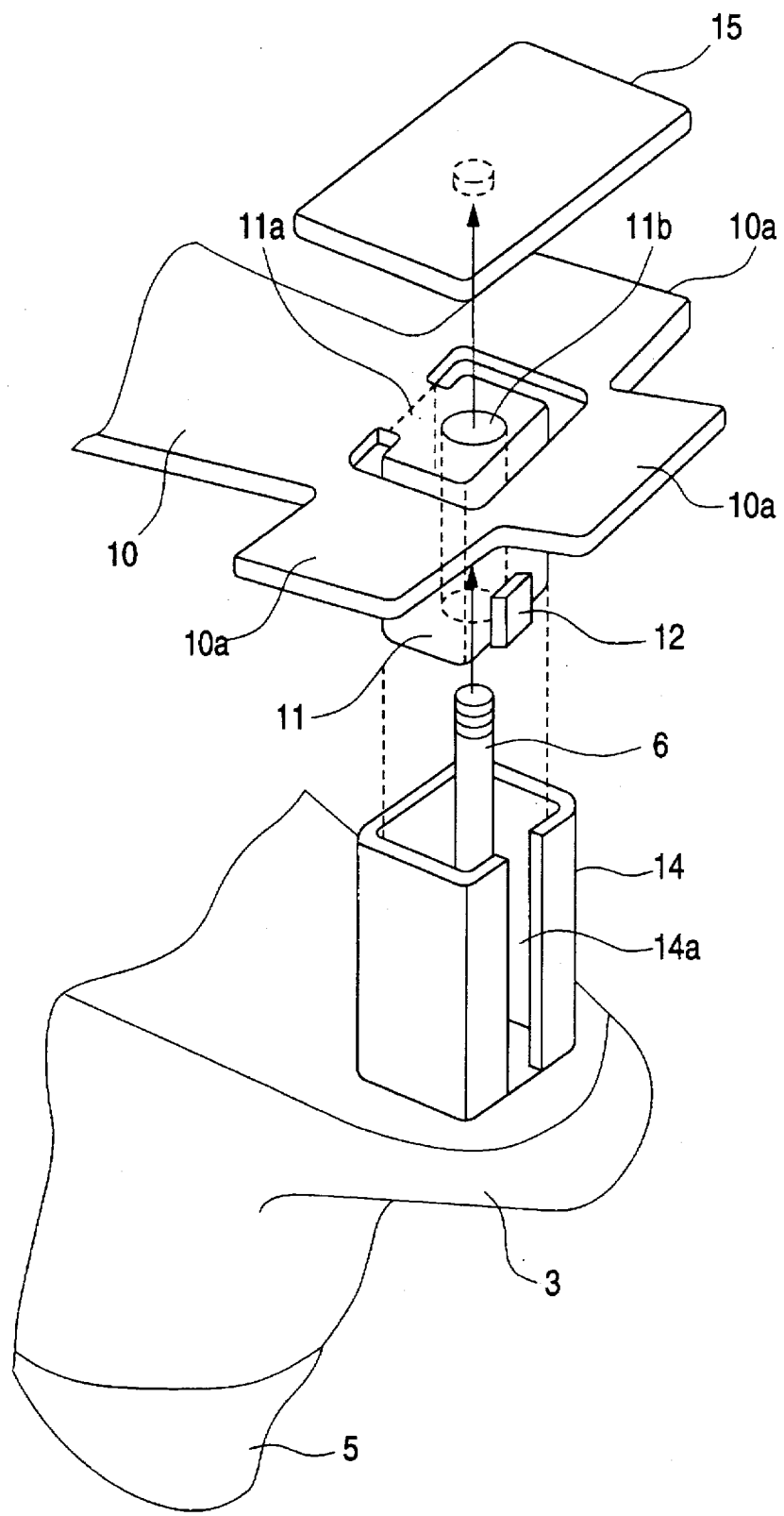
FIG. 2 is an exploded perspective view showing the configuration of the main portion of the tissue transmitted light sensor of FIG. 1.
Figure 3:
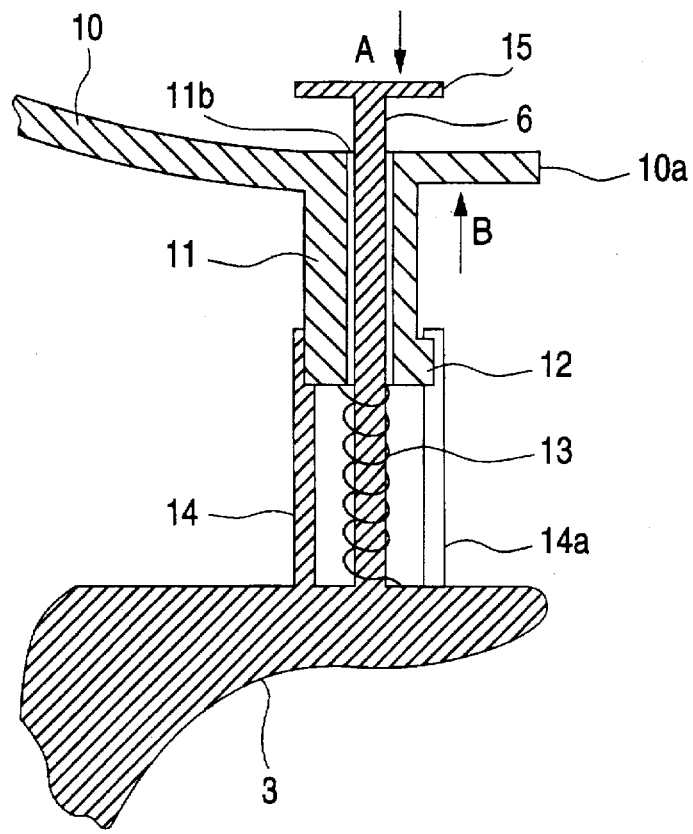
FIGS. 3(a) and 3(b) show section views illustrating the structure for connecting an external auditory canal arm with a holding arm shown in FIG. 1.
Figure 3:
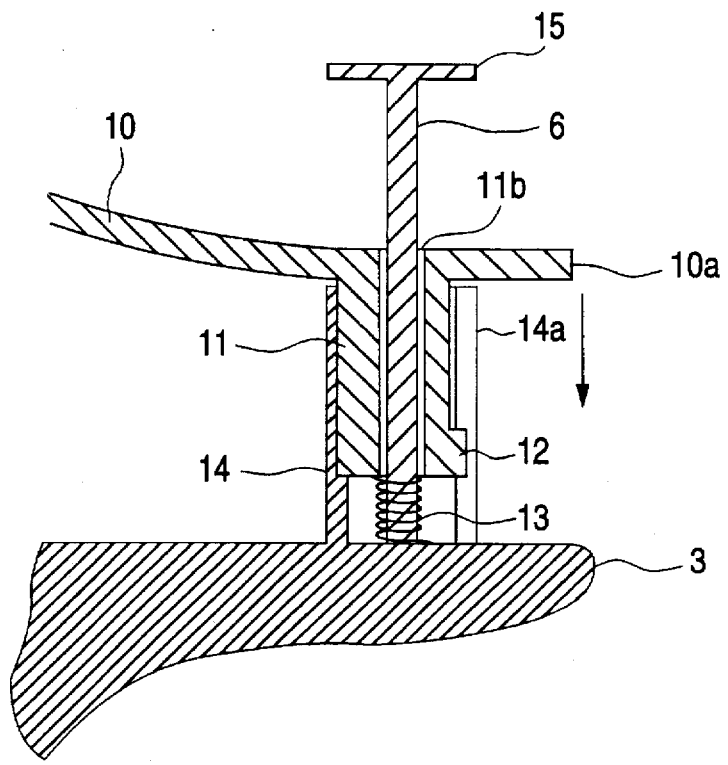

FIGS. 1 to 3 show the configuration of the embodiment of the invention.

In FIGS. 1 and 2, an LED 4 which serves as the light emitting unit is disposed on the upper face of an external auditory canal arm 3 which is to be inserted into an external auditory canal 2 via a cavum conchae 1. The upper face of the external auditory canal arm 3 is formed as a curved face of a shape which conforms to that of the inner face of the external auditory canal 2, and is provided with non-slip processing such as a suede form. A sponge member 5 which elastically abuts against the inner face of the external auditory canal 2 is disposed on the lower face of the external auditory canal arm 3. A supporting shaft 6 stands in a substantially perpendicular direction at one end of the external auditory canal arm 3 which protrudes outwardly from the cavum conchae 1.

A PD 7 which serves as the light receiving unit is disposed on an attaching portion 8 so as to oppose the LED 4. The attaching portion 8 is rotatably held by one end of a holding arm 10 via a shaft 9. A flange 10a which protrudes in three directions as shown in FIGS. 2 and 3 is integrally formed at the other end of the holding arm 10. A prismatic or circular column 11 protrudes downwardly from the center portion of the area of the holding arm 10 where the flange 10a is formed. A part of the column 11 is connected to the holding arm 10 via a connecting part 11a. A projection (stopper) 12 is integrally formed at a lower end of the outer face of the column 11. A through hole 11b is formed so as to pass through the center of the column 11 in the axial direction. The shape of the through hole 11b is similar to the section shape of the supporting shaft 6.

On the other hand, a coil spring 13 is wound around the supporting shaft 6 which stands at the one end of the external auditory canal arm 3. The ends of the coil spring are engaged with the external auditory canal arm 3 and the column 11, respectively. A cover 14 is integrally formed on the external auditory canal arm 3 so as to surround the supporting shaft 6 and the coil spring 13. The column 11 can be fitted into the cover 14 so as to be slidable (movable) in the axial direction. A guide groove 14a into which the projection 12 formed on the column 11 is fitted is formed in the cover 14 so as to elongate in the axial direction. When the supporting shaft 6 is passed through the through hole 11b of the column 11, the projection 12 is engaged with the guide groove 14a so that the column 11 is prevented from being rotated with respect to the cover 14. A flange 15 is screwed to the upper end of the supporting shaft 6.

In the tissue transmitted light sensor configured as described above, when the flanges 10a and 15 are nipped by fingers and pressed in the directions of arrows A and B as shown in FIG. 3(a), the external auditory canal arm 3 and the holding arm 10 are separated from each other. Under this state, the external auditory canal arm 3 is inserted into the external auditory canal 2. When the external auditory canal arm 3 and the holding arm 10 are thereafter released, as shown in FIG. 3(b), the urging force of the coil spring 13 causes the external auditory canal arm 3 and the holding arm 10 to be attracted to each other so as to be close together. As a result, as shown in FIG. 1, the attaching portion 8 is closely attached to the surface of the temporal artery, thereby completing the attaching operation. When the LED 4 emits light, the PD 7 can detect light which transmits the vicinity of the superficial temporal artery.

In the embodiment, the external auditory canal arm 3 and the holding arm 10 are connected to each other via the supporting shaft 6 so as to be slidable (movable) in the axial direction. Even when the space in the ear concha of the subject is different in size among individuals, the angle of the holding arm 10 with respect to the external auditory canal arm 3 is kept substantially constant so that the attaching portion 8 held by the holding arm 10 is prevented from slipping off, thereby enabling the sensor to be stably attached. In the above, the embodiment in which the supporting shaft 6 has a circular column-like shape has been described. Alternatively, the supporting shaft 6 may have a prismatic or elliptical column-like shape and the through hole 11b may have a shape conforming to that of the supporting shaft. In the alternative, the holding arm 10 can be prevented from being rotated with respect to the external auditory canal arm 3, and hence the projection 12 formed on the column 11, and the guide groove 14a formed in the cover 14 are not necessary.

As described above, according to the tissue transmitted light sensor of the invention, since the external auditory canal arm and the holding arm are connected to each other via the supporting shaft so as to be movable in an axial direction, the angle formed by the external auditory canal arm and the holding arm is kept substantially constant so that the attaching portion is prevented from slipping off, thereby enabling the sensor to be stably attached.

What is claimed is:

1. A tissue transmitted light sensor comprising:

an external auditory canal arm which holds one of a light emitting unit and a light receiving unit, said external auditory canal arm adapted to be inserted into an external auditory canal of an ear of a subject;

an attaching portion holding the other one of said light emitting unit and said light receiving unit, said attaching portion adapted to be attached on an outer face of a temporal artery in the vicinity of the ear;

a supporting shaft which is arranged proximate to one end of said external auditory canal arm;

a holding arm rotatably holding at one end said attaching portion and having a column at the other end, a through hole being formed in said column, said supporting shaft being inserted into said through hole so as to be slidable in an axial direction; and a spring wound around said supporting shaft and connecting said external auditory canal arm with said holding arm.

2. The tissue transmitted light sensor as claimed in claim 1, wherein an angle defined by said external auditory canal arm and said holding arm is kept substantially constant.

* * * * *